July 5, 1966 R. E. SNYDER Plant Pat. 2,65
APPLE TREE
Filed Feb. 17, 1965
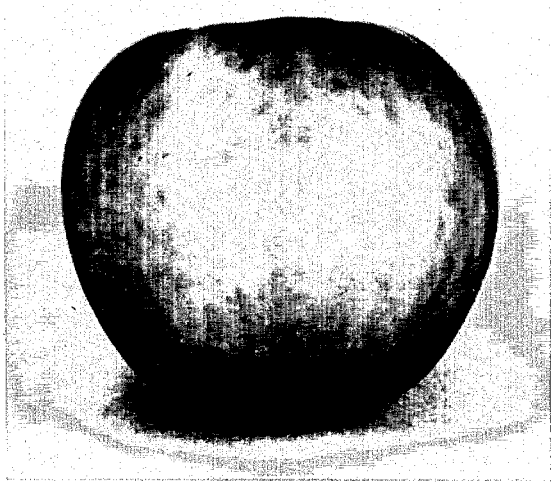
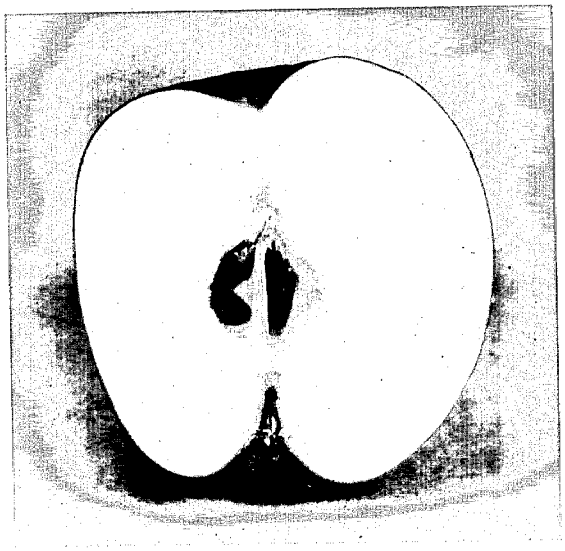
Inventor.
Robert E. Snyder
By: Robert Cobb
Attorneys United States Patent Office Plant Pat. 2,650
Patented July 5, 1966

2,650
APPLE TREE

Robert E. Snyder, Wenatchee, Wash., assignor to Columbia & Okanogan Nursery Co., Inc., Wenatchee, Wash., a corporation of Washington Filed Feb. 17, 1965, Ser. No. 433,527
1 Claim. (Cl. Plt.—34)

The present invention relates to a new and distinct variety of apple tree which was discovered by me as a limb sport in the orchard of my assignee, located near East Wenatchee, Washington.

At the time of my initial discovery of the sport referred to above, I was inspecting the apple crop being grown in the orchard aforementioned under my supervision, and my attention was attracted to a limb on one tree of the apple variety known as "Blackjon" (unpatented) which bore apples having considerably more color than the fruit on the remainder of the tree, Further close inspection of the particular tree referred to in the foregoing, and continued observations of the sport limb, including the fruit borne thereby, for several seasons, convinced me that the earlier coloring characteristics of the fruit definitely differentiated the sport from its parent variety "Blackjon" as well as from all other varieties of which I am aware. That this coloring feature is fixed and comes true by asexual reproduction has been confirmed by fruit borne by second and third generation trees produced by budding in the orchard of my assignee near East Wenatchee, Washington, and by grafting in additional orchards at Brewster, Washington.

The new sport referred to above is definitely new and distinct by reason of the fact that from the standpoint of both the tree and the fruit, it generally resembles the variety "Blackjon," but it is particularly distinguished therefrom by an earlier coloring habit of the fruit, with the full color being attained at least ten days to two weeks earlier than the fruit of "Blackjon," and as a consequence, the trees produce a greater percentage of extra fancy colored fruit at the time of picking, and a much greater percentage of fruit color in the more shaded parts of the tree than is characteristic of the "Blackjon" variety.

The accompanying drawing shows typical specimens of the fruit of my new variety, with one of the specimens being shown in cross section to expose the interior details thereof, and another specimen being depicted in side elevation to illustrate the form and exterior color of the fruit at a stage approximately ten days before attainment of the finishing color.

The following is a detailed description of the new variety, with color terminology in accordance with Koster's Color Guide, except where general color terms of ordinary dictionary significance are obvious, said description being based upon observations made at East Wenatchee, Washington:

Dates of first and last pickings: Same as "Blackjon."

Tree: Medium size; medium vigor; spreading; round topped; medium growing; hardy; productive; regular bearer.

*Trunk.*—Medium stockiness; shaggy.

*Branches.*—Medium thickness; medium smoothness; branching. Color—gray green. Lenticels—few; small.

*Leaves.*—Size—medium. Length—medium. Width—medium. Shape—ovate; taper pointed. Thickness—medium. Surface—smooth. Color—medium green. Margin—crenate; finely serrate. Petiole—medium thickness; medium length.

Flowers: Medium early as compared with other varieties, with dates of first and full bloom the same as the standard "Jonathan" variety (unpatented).

*Size.*—Large.

*Color.*—Pink.

Fruit:

*Maturity when described.*—Hard ripe (date about September 5).

*Size.*—Variable. Axial diameter—from about 2½ inches to 3 inches. Transverse diameter—from about 2 inches to 2½ inches.

*Form.*—Uniform; compressed laterally; truncate at base.

*Cavity.*—Symmetrical; from acute to acuminate; slightly furrowed. Depth—about ⅜ inch. Breadth—from about ½ inch to ⅝ inch.

*Basin.*—Abrupt; wide base.

*Stem.*—Medium stoutness; pubescent.

*Calyx*—Closed (outer surface pubescent).

*Eye.*—Small; partially closed.

*Skin.*—Thin; tough; smooth; glossy; waxed. Dots—obscure; small. Distribution—widely scattered. Color—near Sulphury White, Plate 3. Ground color—substantially solid color near Amaranth Red, Plate 43.

*Bloom.*—Abundant.

*Flesh.*—Juicy. Color—near Creamy White, Plate 2. Texture—firm; crisp. Flavor—subacid. Aroma—pronounced. Quality—good.

*Core.*—Median. Halves of core—equal.

Seeds:

*Number*—Numerous; rather large size.

*Color.*—Near Van Dyck Brown, Plate 96.

Use: Market; dessert.

Keeping quality: Medium, keeps approximately sixty days in ordinary storage.

I claim:

A new and distinct variety of apple tree, substantially as herein shown and described, characterized particularly as to novelty by a general resemblance of the tree and fruit to the variety "Blackjon" (unpatented), but being particularly distinguished therefrom by an earlier coloring habit of the fruit, with the full color being attained at least ten days to two weeks earlier than the fruit of "Blackjon" and resulting in a greater percentage of extra fancy colored fruit at the time of picking and a much greater percentage of fruit color in the more shaded parts of the tree than is characteristic of the "Blackjon" variety.

No references cited.

ABRAHAM G. STONE, *Primary Examiner.*

ANTONIO F. GUIDA, *Examiner.*

R. E. BAGWILL, *Assistant Examiner.*